United States Patent [19]

Berges

[11] 4,094,881

[45] June 13, 1978

[54] PROCESS FOR PREPARING TRIAZOLETHIOLS

[75] Inventor: David A. Berges, Wayne, Pa.

[73] Assignee: SmithKline Corporation, Philadelphia, Pa.

[21] Appl. No.: 751,243

[22] Filed: Dec. 16, 1976

Related U.S. Application Data

[63] Continuation of Ser. No. 665,607, Mar. 10, 1976, abandoned.

[51] Int. Cl.$^2$ ............................................. C07D 249/04
[52] U.S. Cl. .............................. 260/308 A; 260/308 C
[58] Field of Search ..................... 260/308 A, 308 C

[56] References Cited

U.S. PATENT DOCUMENTS 3,867,380   2/1975   Dunn et al. .................... 260/243 C

OTHER PUBLICATIONS

Goerdeler et al., Ber. Dent. Chem., vol. 99, pp. 1618–1631 (1966).
Begtrup, Chem. Abstracts, vol. 76, Abstract No. 72454t (1972).
Dunn et al., Chem. Abstracts, vol. 84, Abstract No. 159507b (1976).

*Primary Examiner*—Alton D. Rollins
*Attorney, Agent, or Firm*—Janice E. Williams; William H. Edgerton; Alan D. Lourie

[57] ABSTRACT

1,2,3-Triazole-4(5)-thiol is prepared by treating 1-benzyl-1,2,3-triazole with a strong base, treating the resulting anion with sulfur, removing the benzyl group by reductive means, and acidifying the resulting thiolate with strong acid.

8 Claims, No Drawings

PROCESS FOR PREPARING TRIAZOLETHIOLS

This is a continuation of application Ser. No. 665,607 filed Mar. 10, 1976, now abandoned.

This invention relates to a chemical process. In particular, the invention relates to a chemical process for preparing 1,2,3-triazole-4(5)-thiol of Formula I. This thiol may exist in several tautomeric forms and the structure of Formula I is used for illustration only. It is intended that this invention comprehend the 1H-tautomer of 1,2,3-triazole-4(5)-thiol and its 2H and 3H-tautomers, as well as their thione tautomers.

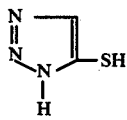
I 1,2,3-Triazole-4(5)-thiol is a known compound [Chem. Ber. 99 (5), 1618-31 (1966)]. It is useful as an intermediate for preparing the antibacterial cephalosporin compound cefatrizine, 7-(α-amino-p-hydroxyphenylacetamido)-3-(1,2,3-triazol-5-ylthiomethyl)-3-cephem-4-carboxylic acid (U.S. Pat. No. 3,867,380).

The preferred prior method for preparing 1,2,3-triazole-4(5)-thiol is that described by Goerdeler and Gnad, Chem. Ber. 99(5), 1618-31 (1966). This method consists of the rearrangement of 5-amino-1,2,3-thiadiazole. The method of the present invention, in contrast, consists of reacting 1-benzyl-1H-1,2,3-triazole (II) with a base sufficiently strong to generate an anion at the 4-position of the triazole ring, reacting the resulting anionic triazole III with sulfur to give a 4-thiolate, removing the benzyl group by reductive means, and treating the resulting thiolate V with acid to give 1,2,3-triazole-4(5)-thiol (I). In the formulas presented, M $^\oplus$ is a cation, preferably of an alkali or alkaline earth metal.

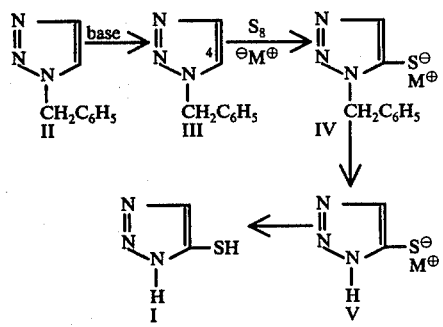

Any base may be used in the reaction with compound II as long as it is strong enough to extract the proton (H$^{30}$) from the ring and generate the anion. Among the bases that may be used are alkyl- or aryl-lithium, potassium and sodium reagents, lithium, potassium or sodium amides and their mono- and dialkyl derivatives and potassium hydride. Alkyl and aryl lithium reagents are preferred.

The most preferred base is butyllithium. The reaction with the base is carried out in an inert organic solvent at a temperature from −90° to 0° C. The preferred temperature is from −78° to −30° C. A temperature of −60° C is convenient. Among the permissable solvents are hexane, petroleum ether, benzene, tetrahydrofuran, ether, dioxane, dialkoxyethanes and mixtures thereof. The reaction is preferably conducted in an inert atmosphere of nitrogen and is essentially instantaneous. A solution of a slight excess of the base is added to a solution of the benzyltriazole II. The resulting solution is stirred for a short time thereafter.

The sulfur is then added in one portion, the mixture is stirred at low temperatures, e.g. −78° C to 0° C, with a temperature between −78° and −30° preferred, for up to about an hour; and the thiolate IV is isolated by pouring the solution into ether and then washing the resulting precipitate with additional ether.

The resulting thiolate IV is then treated in a known manner to remove the benzyl protective group. Among the permissible methods are reductive methods using alkali metals or calcium in liquid ammonia, low-molecular weight aliphatic amines, hexamethylphosphoramide, ethers or alcohols with or without an inert cosolvent such as ether, tetrahydrofuran, etc. Complexing agents such as macrocyclic polyethers can be used advantageously in ethereal solvents. The preferred method uses sodium in liquid ammonia or low-molecular weight amines. The most preferred method utilizes sodium in liquid ammonia. The debenzylated compound V is then acidified to give the product I. Any non-oxidizing strong acid may be used, inorganic or organic, provided that it is a stronger acid than the thiol I. Among the acids that may be used are hydrochloric, sulfuric, acetic, citric.

The 1-benzyl-1,2,3-triazole starting material (II) is a known compound described by T. Curtius and K. Raschig, J. prakt. Chem. 125, 466–97 (1930), also by R. H. Wiley, K. F. Hussing and J. Moffat, J. Org. Chem. 21, 190–192 (1956).

The following example illustrates the practice of the process of the invention, but should not be construed as limiting the scope thereof.

EXAMPLE

1H-1,2,3-Triazole-4(5)-thiol

A solution of n-butyllithium (30 ml., 0.07 mol.) in hexane was added dropwise under nitrogen to a stirred solution of 1-benzyl-1H-1,2,3-triazole (9.5 g., 0.06 mol.) in 120 ml. of dry tetrahydrofuran which had been cooled to −60° C. When the addition was complete the deep orange solution was stirred for another 15 minutes and then sublimed sulfur (1.95 g., 0.06 mol.) was added in one portion. After stirring for 15 minutes at −60° C and 30 minutes at −40° C the dark mixture was poured into 800 ml. of diethyl ether. The mixture was stirred for 30 minutes and the diethyl ether was decanted and replaced with fresh diethyl ether. After washing three more times with diethyl ether the solid was triturated with ethyl acetate, collected and dried to give 11.2 g. (87%) of the lithium salt of the 4-thiol.

$C_9H_8LiN_3S \cdot 1.5 H_2O$ — Calculated: C, 48.21; H, 5.94; N, 18.74. Found: C, 48.26; H, 6.06; N, 18.94.

The lithium salt of 1-benzyl-1H-1,2,3-triazol-4-thiol (20 g., 0.102 mol.) was dissolved in 500 ml. of liquid ammonia and small pieces of sodium (6 g., 0.26 mol.) were added gradually (ca. 1 hour) until a permanent blue color persisted for 5 minutes. The ammonia was allowed to evaporate and the white solid which remained was dissolved in 250 ml. of water. The solution was adjusted to pH to 10–11 with concentrated HCl and extracted with diethyl ether (3 × 50 ml.). The separated aqueous phase was acidified to pH 2.5 with concentrated HCl. extracted with ethyl acetate and the combined dried extracts evaporated to give the title product. An ethyl acetate solution of this product was treated dropwise with 75 ml. of sodium 2-ethylhexanoate solution (30% in isopropyl alcohol). The precipitated white solid was collected, washed with ethyl acetate, then with ether and dried at 60° C to give 9.5 g. (76%) of the sodium salt of the product.

$C_2H_2N_3NaS \cdot 3/4 H_2O$ — Calculated: C, 17.58; H, 2.58; N, 30.75. Found: C, 18.06; H, 3.03; N, 30.49.

I claim:

1. A process for preparing 1,2,3-triazole-4(5)-thiol of the formula:

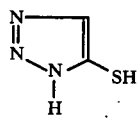

comprising (1) treating 1-benzyl-1H-1,2,3-triazole of the formula

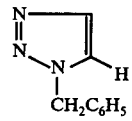

with a base sufficiently strong to generate an anionic charge at the 4-position of said triazole (2) treating the resulting anionic triazole with sulfur to give a 4-thiolate of the formula

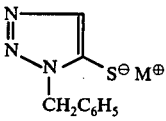

where $M^{\oplus}$ is the cation of said base, (3) removing said benzyl group be reductive means, and (4) acidifying the resulting 4-thiolate with strong acid to give the triazole thiol.

2. A process according to claim 1, in which the base is butyllithium.

3. A process according to claim 1, in which the benzyl group is removed with sodium and liquid ammonia.

4. A process according to claim 1, in which the acid is hydrochloric acid.

5. A process according to claim 1, in which the base is butyllithium, the benzyl group is removed with sodium and liquid ammonia, and the acid is hydrochloric acid.

6. A process for preparing a 1,2,3-triazole-4-thiolate of the formula:

comprising treating 1-benzyl-1H-1,2,3-triazole with a base sufficiently strong to generate an anionic charge at the 4-position of said triazole and then treating the resulting anionic triazole with sulfur to give the 4-thiolate wherein $M^{\oplus}$ is the cation of said base.

7. A process according to claim 6, in which the anionic triazole is treated with sulfur at a temperature of from −78° to 0° C.

8. A process according to claim 7, in which the anionic triazole is treated with sulfur for up to about 1 hour.

* * * * *